US012485275B2

(12) United States Patent
Atkin et al.

(10) Patent No.: US 12,485,275 B2
(45) Date of Patent: Dec. 2, 2025

(54) MEDICAL TREATMENT DEVICE AND METHOD OF OPERATION THEREOF

(71) Applicant: NEUROTONE AUSTRALIA PTY LTD, Bentleigh (AU)

(72) Inventors: Brendan Atkin, Bentleigh (AU); Allison Atkin, Bentleigh (AU)

(73) Assignee: NEUROTONE AUSTRALIA PTY LTD, Bentleigh (AU)

( * ) Notice: Subject to any disclaimer, the term of this patent is extended or adjusted under 35 U.S.C. 154(b) by 591 days.

(21) Appl. No.: 17/762,061

(22) PCT Filed: Sep. 21, 2020

(86) PCT No.: PCT/AU2020/000106
§ 371 (c)(1),
(2) Date: Mar. 19, 2022

(87) PCT Pub. No.: WO2021/051152
PCT Pub. Date: Mar. 25, 2021

(65) Prior Publication Data

US 2022/0370786 A1 Nov. 24, 2022

(30) Foreign Application Priority Data

Sep. 20, 2019 (AU) ................................ 2019903506

(51) Int. Cl.
*A61N 1/04* (2006.01)
*A61N 1/36* (2006.01)

(52) U.S. Cl.
CPC ......... *A61N 1/0456* (2013.01); *A61N 1/0404* (2013.01); *A61N 1/36021* (2013.01)

(58) Field of Classification Search
CPC ................ A61N 1/0456; A61N 1/0404; A61N 1/36021; A61N 1/36025; A61N 1/0472; A61N 1/36036; A61N 1/36034
See application file for complete search history.

(56) References Cited

U.S. PATENT DOCUMENTS

2007/0250145 A1* 10/2007 Kraus ................ A61N 1/36017 607/136
2008/0249594 A1* 10/2008 Dietrich ............... A61H 39/002 600/382

FOREIGN PATENT DOCUMENTS

WO WO-2016109851 A1 * 7/2016 ............ A61M 21/00

* cited by examiner

*Primary Examiner* — Gary Jackson
*Assistant Examiner* — Sebastian X Lukjan
(74) *Attorney, Agent, or Firm* — Bochner PLLC; Andrew Bochner; Eric Kleinertz

(57) ABSTRACT

There is disclosed a system for providing transcutaneous electrical stimulation to the vagus nerve of an individual comprising: an electrode unit mountable within the auricle of the individual and having at least a first electrode and a second electrode for applying the transcutaneous electrical stimulation at the cymba conchae and the tragus of the individual's auricle, and a controller for controlling the transcutaneous electrical impulse delivered by each of the first electrode and second electrode.

15 Claims, 5 Drawing Sheets

MEDICAL TREATMENT DEVICE AND METHOD OF OPERATION THEREOF

RELATED APPLICATIONS

The present application claims priority from Australian Provisional Patent Application No. 2019903506 filed on 20 Sep. 2019, the entire contents of which are incorporated herein by reference.

FIELD OF INVENTION

The present invention relates generally to a device and method for applying a medical treatment, and in particular, to a non-invasive device and method for applying medical treatment by way of electrical stimulation to the vagus nerve of an individual.

BACKGROUND OF THE INVENTION

The use of electrical stimulation patterns or regimes to treat medical conditions is well known and has been applied across a variety of different medical applications. Pacemakers have long been established as a lifesaving device for those suffering from heart conditions whereby an implanted stimulator is able to be controlled to deliver electrical stimulation to the heart tissue by way of one or more electrodes positioned to be in direct contact with the heart tissue.

Whilst for a different purpose than pacemakers, cochlear implants have also been developed to be implanted within the cochlear of individuals having impaired hearing to use electrical stimulation to bypass the natural processes of the cochlear to electrically stimulate the auditory nerves to replicate external sounds and noises. Numerous other implantable electrical devices have also been developed which harnessing electrical stimulation for application to an individual to treat conditions such as epilepsy, dementia and other such conditions.

Whilst the above referenced systems and methods of applying electrical stimulation to treat specific patient conditions have been proven very successful, they are specific to treating a specific problem and use invasive devices and require components to be implanted within the patient's body.

There are many other examples whereby electric stimulation has been used to treat a variety of different medical conditions via non-invasive means. In the field of physiotherapy, electrical stimulation of muscles has long been used to strengthen weak muscles and improve muscle tone, particularly for rehabilitation purposes. This is typically referred to as Electrical Muscle Stimulation (EMS) and uses electrical stimulation to cause muscle contraction achieved by placing electrodes on the skin of the individual, adjacent the muscles to be to be stimulated. The electrodes are typically in the form of pads that adhere to the skin and the electrical impulses they elicit are configured to mimic the natural action potential that comes from the central nervous system of the individual to contract the muscle.

Another common form of electrical stimulation that is used to treat a variety of medical conditions is referred to as Transcutaneous Electrical Nerve Stimulation (TENS). Like EMS, TENS is a non-invasive system that uses an externally located electrode pad to deliver an electrical impulse through the skin. However, the electrical impulse delivered by the TENS system is intended to stimulate the nerves of the user, rather than the muscles. TENS is often used to treat pain experience by the user, such as pain associated with rheumatoid arthritis, osteoarthritis as well as low back pain, neck pain or knee pain. This is achieved through the application of stimulation to the nerves of the user adjacent the pain site to prevent pain signals from reaching the brain. It is considered that the application of such stimulation may also relax muscles and release endorphins that function as natural painkillers.

In more recent times, especially with increased and more mainstream medical use of EMS and TENS, greater research and understanding has been obtained into electrical stimulation in specific regions of the body, such as the vagus nerve. The vagus nerve is the longest and most complex of the cranial nerves and enables the brain to monitor and receive information about several of the bodies different functions, typically associated with the neck, heart, lungs and abdomen together with its several systemic efferent functions. Much research has been undertaken with regard to the role the vagus nerve may play in relation to the treatment of a variety of different conditions ranging from anxiety disorders, headaches, migraines, inflammatory conditions, obesity, alcohol addiction, chronic heart failure, autoimmune disorders, epilepsy and autism.

Early attempts to stimulate the vagus nerve involved implanting a stimulator in a patient's chest and tunnelling electrodes up through the patient's neck so as to wrap around the vagus nerve for stimulation. Such a stimulation system was used to treat epilepsy by sending electrical stimulation at regular intervals to the brain via the vagus nerve to reduce the severity of seizures and in some instances it was found to stop seizures. Whilst the system has been successful in treating the condition in some cases, it is a very invasive procedure and may not be suitable for use in all patients suffering from such afflictions.

In more recent times, non-invasive systems have been introduced for stimulating the vagus nerve. Such systems have sought to target the outer ear where the auricular branch of the vagus nerve is located, with the stimulator placed to stimulate the cymba conchae of the ear. As the auricular branch of the vagus nerve innervates the cymba conchae, it has been considered that applying stimulation directly to the cymba conchae of the ear, effective stimulation of the vagus nerve can be achieved.

The present invention is seeking to develop this concept further to provide a body worn device that can be worn by a user to provide more targeted stimulation of the vagus nerve to address a number of medical conditions.

The above references to and descriptions of prior proposals or products are not intended to be, and are not to be construed as, statements or admissions of common general knowledge in the art. In particular, the above prior art discussion does not relate to what is commonly or well known by the person skilled in the art, but assists in the understanding of the inventive step of the present invention of which the identification of pertinent prior art proposals is but one part.

STATEMENT OF INVENTION

The invention according to one or more aspects is as defined in the independent claims. Some optional and/or preferred features of the invention are defined in the dependent claims.

Accordingly, in one aspect of the invention there is provided a system for providing transcutaneous electrical stimulation to the vagus nerve of an individual comprising:

an electrode unit mountable within the auricle of the individual and having at least a first electrode and a second electrode for applying the transcutaneous electrical stimulation at the cymba conchae and the tragus of the individual's auricle;

a controller for controlling the transcutaneous electrical impulse delivered by each of the first electrode and second electrode.

In a preferred embodiment the transcutaneous electrical stimulation may be applied to the auricular branch of the vagus nerve of the ear. The electrical stimulation may include transmission of the electrical impulse applied to the auricular branch of the vagus nerve of the ear to central brain projections.

The waveform of the electrical stimulation supplied by the controller may be asymmetric. The waveform of the electrical stimulation supplied by the controller may be biphasic. The waveform of the electrical stimulation supplied by the controller may be sinusoidal.

The controller may be able to control the pulse rate of the electrical stimulation applied by the electrodes. The controller may be able to control the pulse width of the electrical stimulation applied by the electrodes. The controller may be able to control the pulse amplitude of the electrical stimulation applied by the electrodes.

The electrode unit may comprise a moulded body configured to be mounted within the auricle of the individual. The first electrode and the second electrode may be mounted within the moulded body. Each of the first electrode and second electrode may be mounted within a housing that is movably mounted to the moulded body to facilitate adjustment of the position of the first and second electrodes with respect to the vagus nerve.

The moulded body may be made of a semi-flexible material. The moulded body may be formed in a variety of different sizes to accommodate different sized auricles. The moulded body may be made of a material including silicone.

The moulded body may include a first and a second recess for receiving the first and second electrode respectively. The moulded body may have at least one projecting portion for projecting into the ear of the individual to aid in retaining the electrode unit in position. The at least one projecting portion may project into the ear canal of the ear of the individual.

In another aspect, there is provided a method of stimulating the auricular branch of the vagus nerve of an individual for treatment of a medical condition comprising:

positioning a first stimulator adjacent a cymba conchae of the individual;

positioning a second stimulator adjacent an inner surface of a tragus of the individual;

applying electrical stimulation between the first and the second stimulators at a predetermined frequency and pulse duration for a predetermined period.

In an embodiment of this aspect of the invention, the electrical stimulation is applied between the first and second stimulators at a frequency of 25 Hz, pulse duration of 500 μs with an alternating cycle for a period of 10 minutes.

BRIEF DESCRIPTION OF THE DRAWINGS

The invention may be better understood from the following non-limiting description of preferred embodiments, in which.

DETAILED DESCRIPTION OF THE DRAWINGS

Preferred features of the present invention will now be described with particular reference to the accompanying drawings. However, it is to be understood that the features illustrated in and described with reference to the drawings are not to be construed as limiting on the scope of the invention.

The system and method of the present invention will be described below in relation to a non-invasive device for applying therapeutic stimulation of the vagus nerve via the external ear. However, it will be appreciated that the system and method of the present invention could also be achieved by applying stimulation to the vagus nerve at other sites, using either an invasive or minimally invasive stimulation system.

The present invention is primarily directed towards addressing inflammation issues in the human body. It is based on an understanding that communication between the immune system and the brain is vital for controlling inflammation. The inflammatory reflex is a centrally integrated physiological mechanism in which afferent vagus nerve signalling, activated by cytokines or pathogen-derived products, is functionally associated with efferent vagus nerve-mediated output to regulate pro-inflammatory cytokine production and inflammation. The present invention utilises this physiological reflex and system and stimulates the regions of the brain responsible for this reflex, actively regulating pro-inflammatory cytokines.

Figure 1:
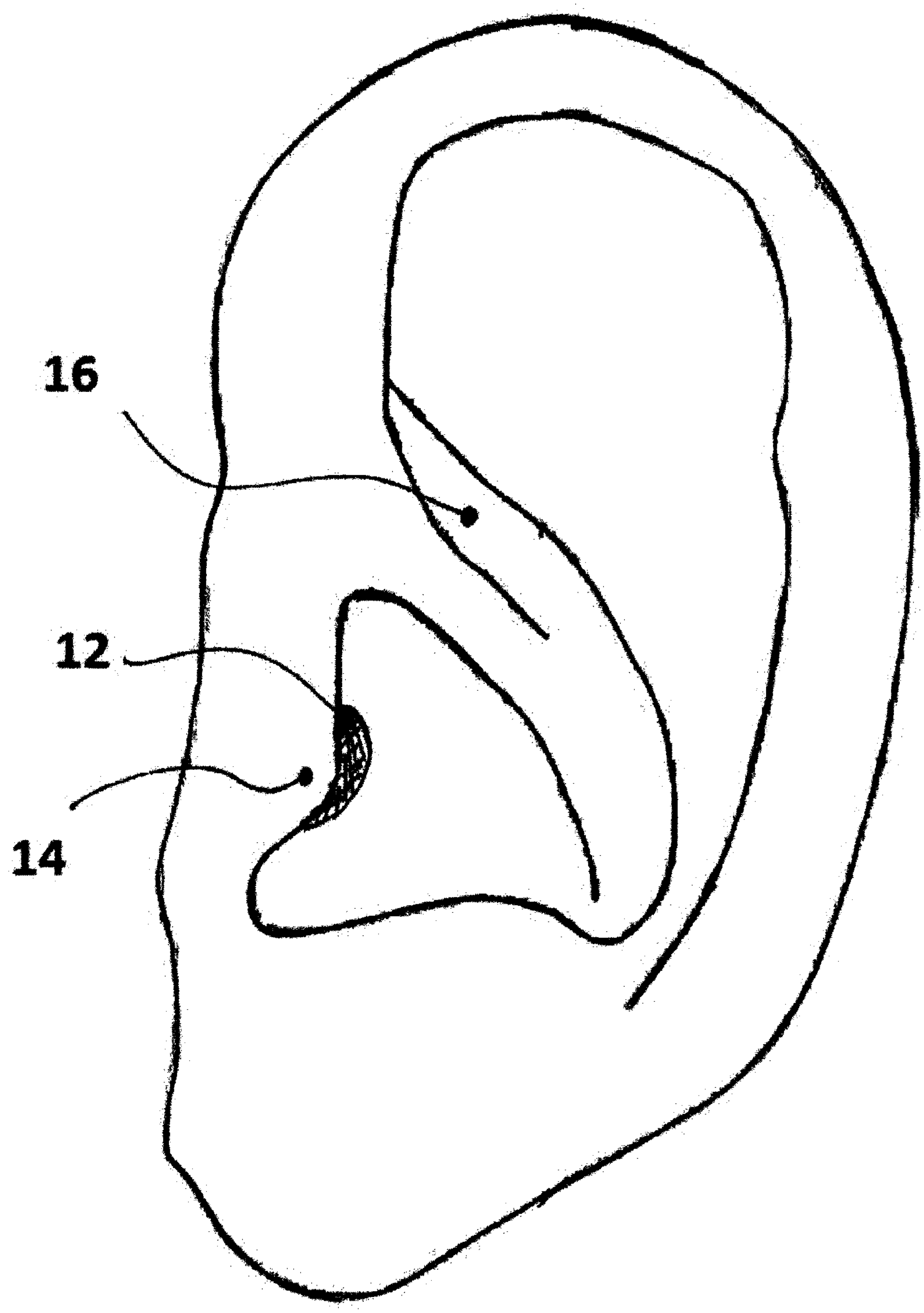
FIG. 1 is a view of an auricle of a user suitable for using the present invention.

Referring to FIG. 1, an auricle or external ear 10 of a human is depicted for use with the present invention. The vagus nerve is one of the cranial nerves that connects the brain to the body and can be generally thought of as a circuit that links the neck, heart, lungs and abdomen to the brain. Whilst located internally, the vagus nerve has an auricular branch that supplies afferent sensory innervation from the auricle 10, ear canal 12 and tragus 14. In this regard, the auricular branch of the vagus nerve is distributed to the skin at the back of the auricle and to the posterior part of the ear canal as is shown in FIG. 1. This results in the distribution of the Auricular Branch of the Vagus Nerve (ABVN) to the cymba conchae, and a portion of the area surrounding the auditory meatus, including the inner/antero-medial aspect of the tragus. For the purposes of the present invention reference is also made to the cymba conchae 16 which also provides direct access to the auricular branch of the vagus nerve.

Figure 2:
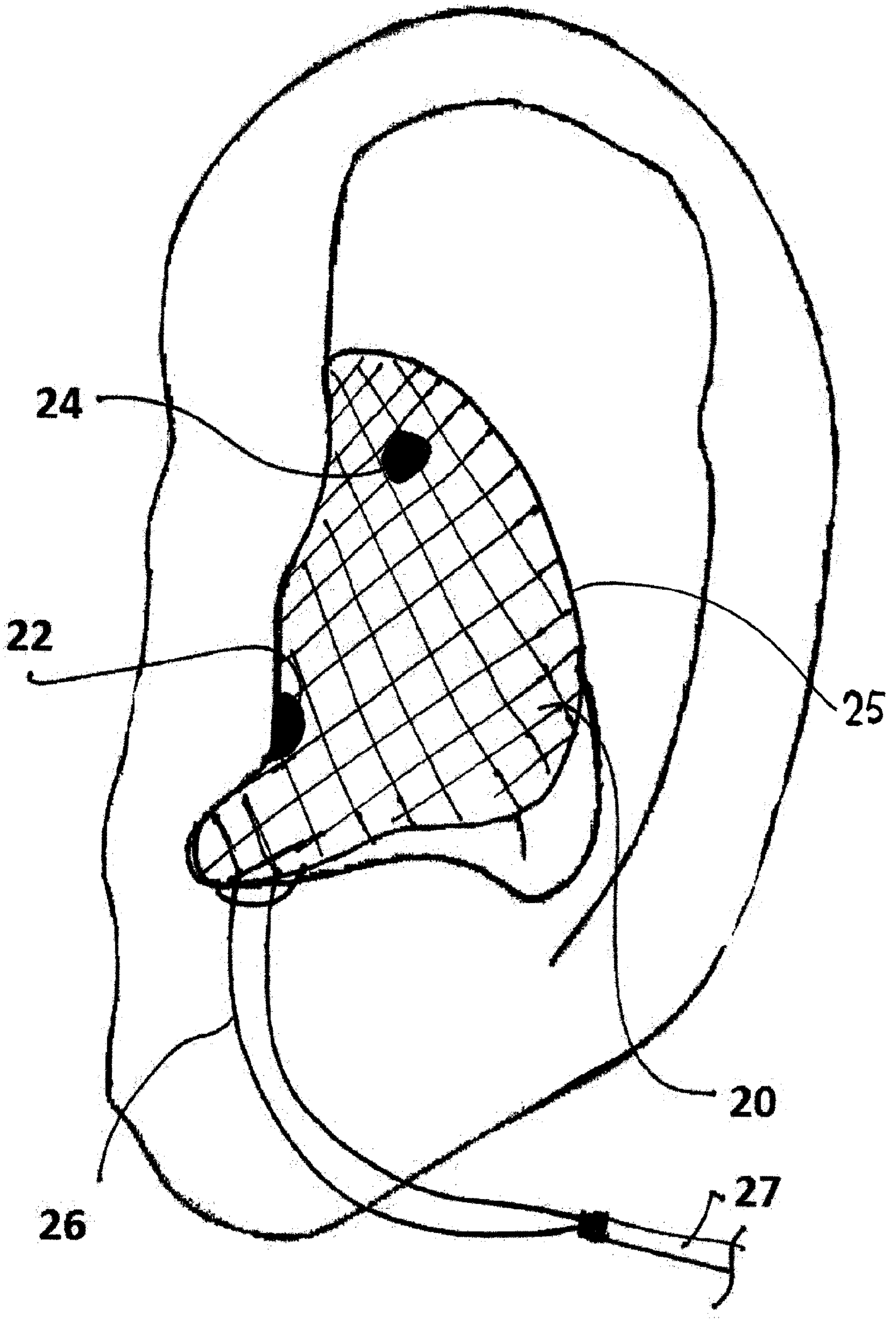
FIG. 2 is a view of the auricle of FIG. 1 with an electrode unit in accordance with an embodiment of the present invention in position.

In accordance with the present invention, in order to best access the vagus nerve, it is considered ideal to apply electrical stimulation to the surface of the auricle adjacent the cymba conchae 16 and the inner surface of the tragus 14, as depicted in FIG. 1. To achieve this, an electrode unit 20 of FIG. 2 is provided.

The electrode unit 20 is in the form of a silicone body 25 adapted to be worn in the external ear 10 of the individual. The silicone body 25 is a mouldable body that is configured to fit within the outer ear of the user in a manner that automatically aligns incorporated electrodes 22, 24 with the tragus 14 and cymba conchae 16 respectively, when the electrode unit 20 is worn. As will be discussed in more detail below, the body 25 has a portion that is adapted to be received within the ear canal 12 of the wearer so as to be retained in position during use in a comfortable and effective manner. In this regard, the body 25 of the electrode unit 20 may be moulded to conform with the outer ear of the user or may be formed in a generic manner with sufficient variability to be used by any individual so as to be effectively and comfortable worn with minimal adaptation.

Figure 3:
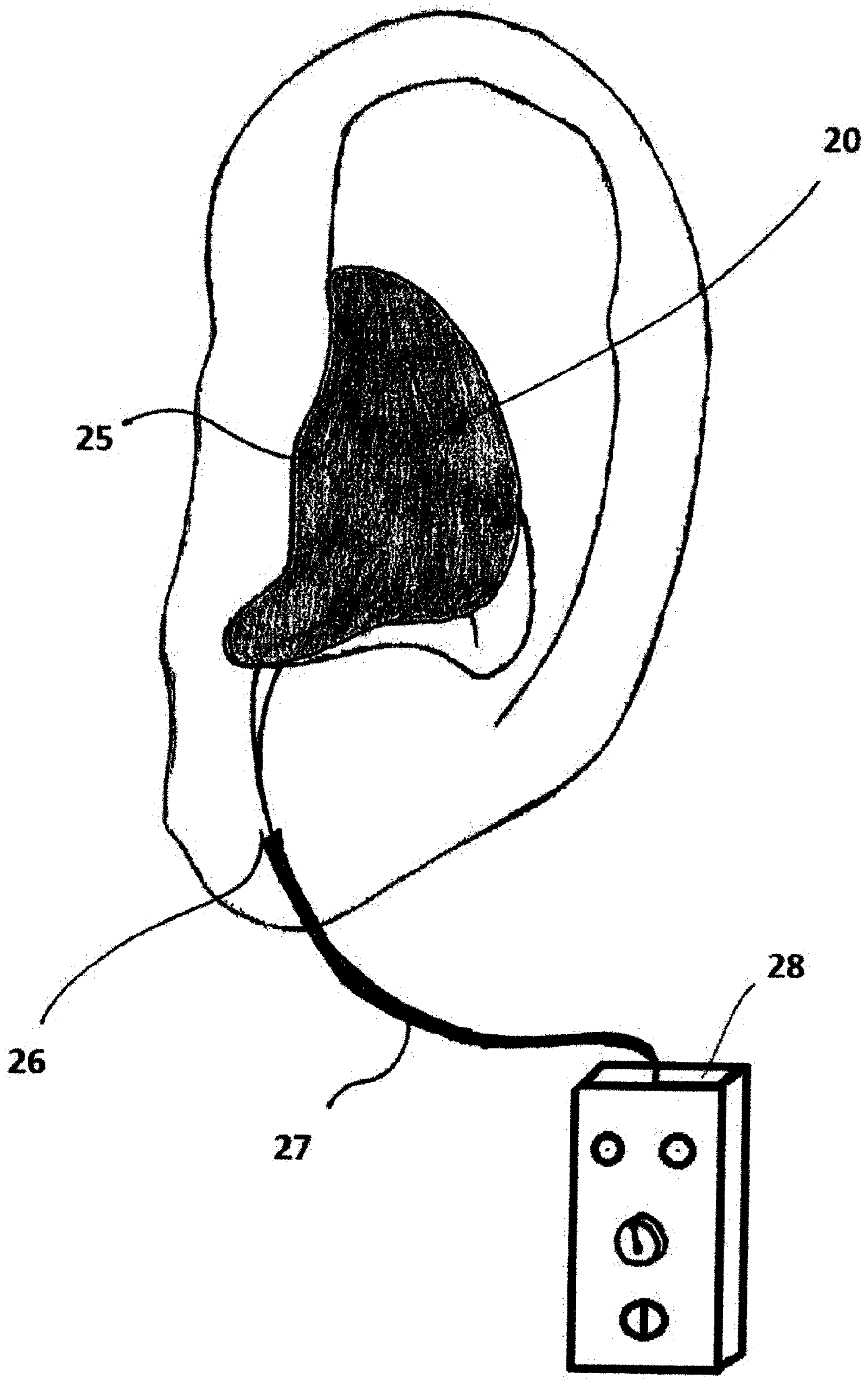
FIG. 3 is a view of a system for providing transcutaneous electrical stimulation to the vagus nerve in accordance with an embodiment of the present invention.

The electrodes 22 and 24 are in the form of discrete electrode discs positioned at the surface of the body 25 such that when the electrode unit 20 is positioned for use, the electrodes 22, 24 are in contact with the skin surface at the tragus 14 and the cymba conchae 16 for delivery of the stimulation regime to the vagus nerve. Each electrode 22, 24 has a wire 26 connected thereto which extends from a cord 27 to a remotely located stimulator unit 28 which controls and regulates the stimulation applied by the electrodes 22, 24, as shown in FIG. 3. The wires 26 are embedded within the body 25 by way of dedicated tunnels formed therein, as will be described in more detail below.

Alternatively, the electrodes 22, 24 may comprise a transmitter/receiver unit (not shown) to wirelessly connect with a stimulator unit 28 to receive and process the control signals received by the stimulator unit 28 for application. In such an embodiment, the transmitter/receiver unit may also be embedded within the body adjacent the electrodes 22, 24.

In another embodiment, each of the electrodes 22, 24 may be mounted within a housing that is pivotally attached to the body 25 to enable a degree of adjustment by the wearer to correctly position the electrodes 22, 24 at the desired stimulation site. The electrodes 22, 24 may be mounted to an extremity of the housing so as to be positioned directly against the wearer's skin.

The stimulator unit 28 may be in the form of a conventional TENS/EMS control unit that is capable of controlling the frequency and amplitude of the stimulation applied by each electrode 22, 24 and may be programmed or adjusted according to the individual user's requirements.

Figure 4:
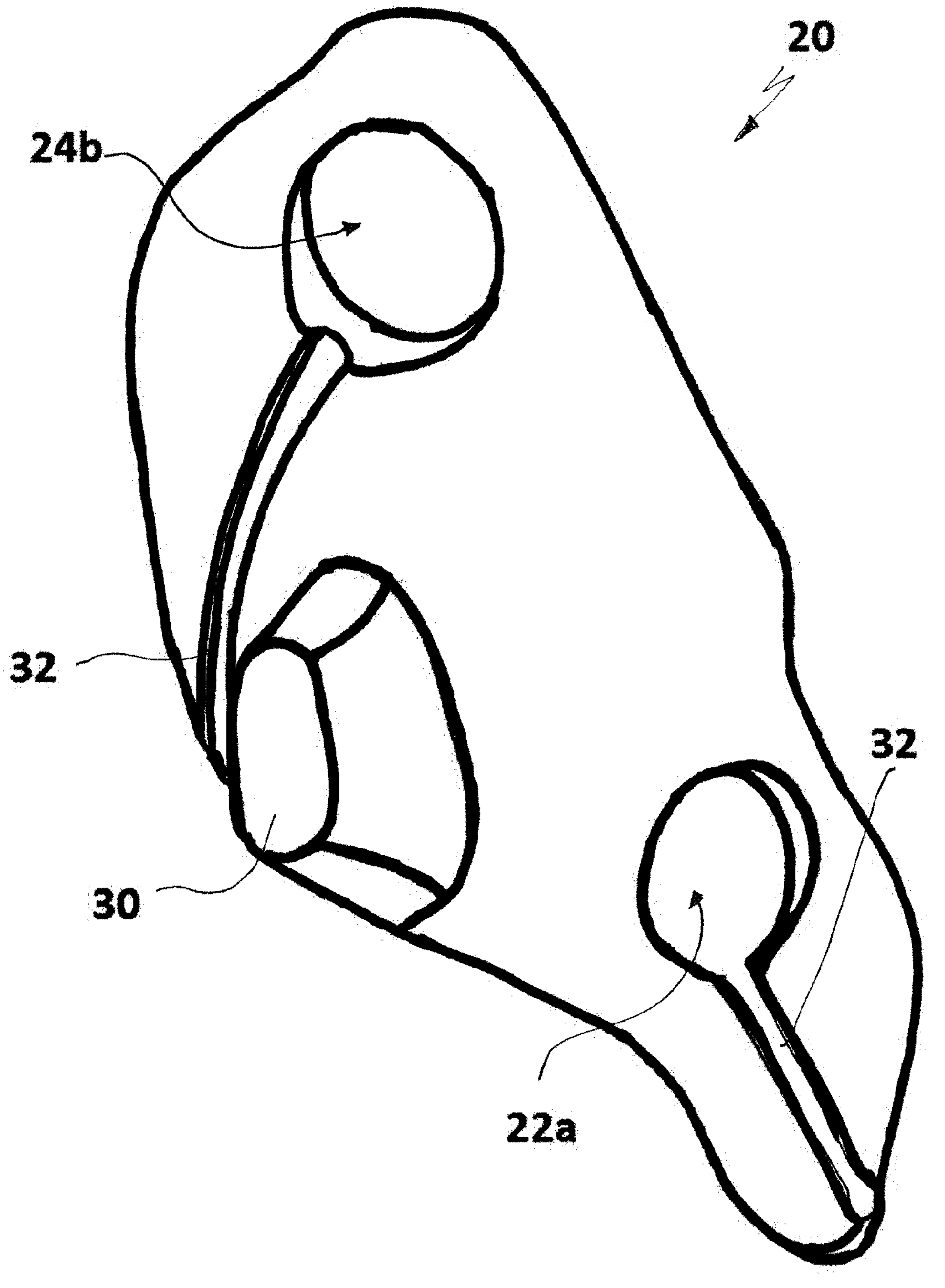
FIG. 4 is a perspective view of an embodiment of an electrode unit in accordance with the present invention.
Figure 5:
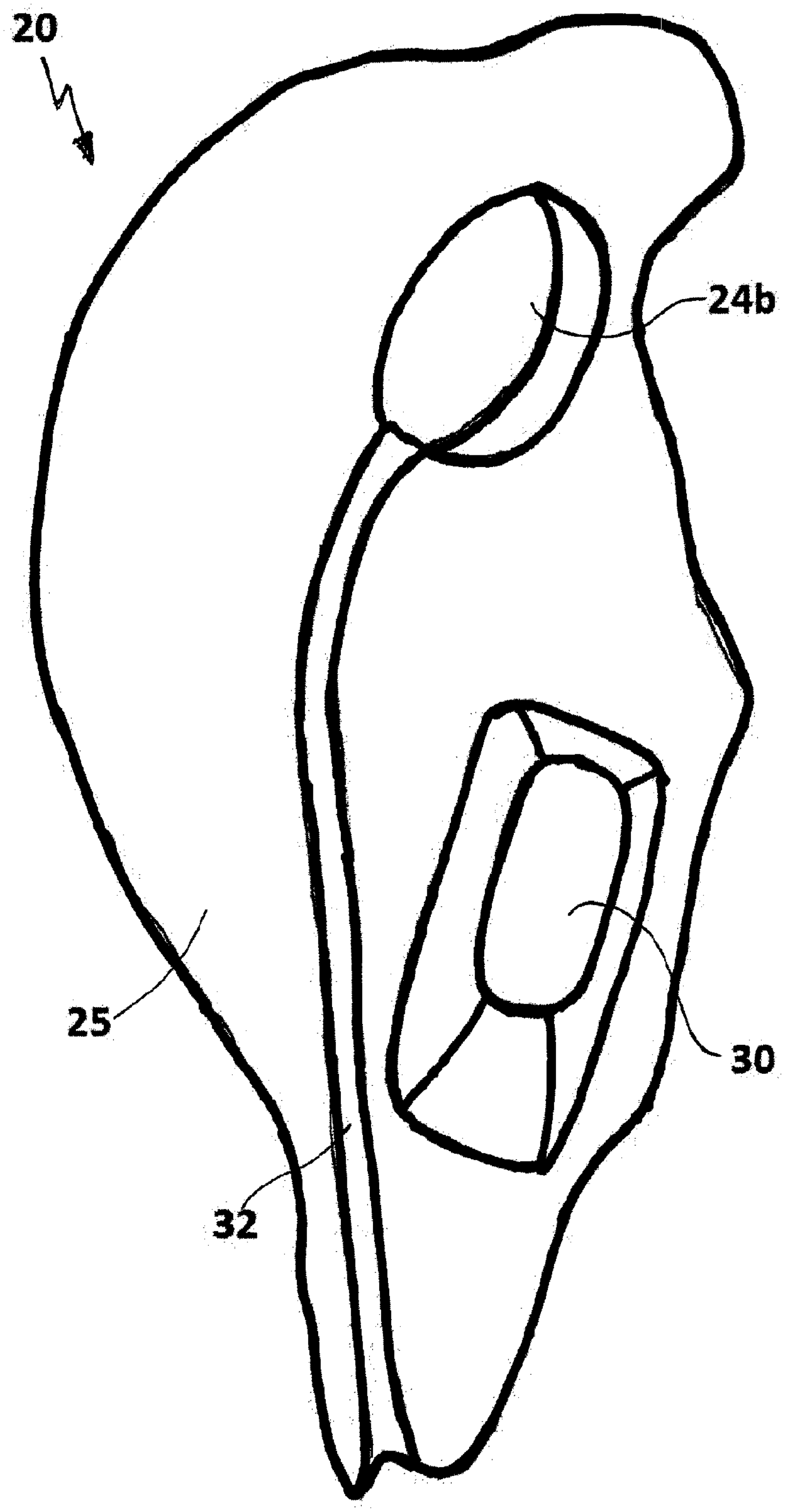
FIG. 5 is a different perspective view of the top view of the electrode unit depicted in FIG. 4.

Referring to FIGS. 4 and 5, alternative views of the electrode unit 20 are shown detailing the manner in which the electrode discs are positioned for use. As is shown, the body 25 is moulded from a silicone or similar material to have recesses 22*a*, 24*a* formed at the appropriate locations to receive and hold the electrodes for use. A projection 30 is formed on the body 25 to be located at least partially within the ear canal 12 of the user to locate and orientate the body 25 in position. When in this position, the electrodes 22, 24 are positioned immediately in contact with the surface of the user's ear adjacent the tragus 14 and cymba concha 16 respectively. This enables the electrical stimulation to be delivered from the electrode surface and to the vagus nerve. Tunnels or channels 32 are formed within the body 25 to accommodate the leads 26 connecting the electrodes 22, 24. The leads 26 each exit the body 25 at a substantially common point to ensure that the unit 20 is comfortably secured in position for use.

It will be appreciated that the body 25 whilst having a common configuration, will be supplied in a variety of sizes to accommodate different sized ears and different ages of users. In such instances, the electrode positions 22, 24 will be the same within the body 25, but the body 25 will be sized differently. It will be appreciated that given the nature of the material used and the shape of the body 25, once it has been appropriately positioned within the user's ear it will be maintained in position due to the fitted interaction of the unit 20 with the user's ear.

The system of the present invention is primarily directed towards providing concentrated vagus nerve stimulation for the treatment of those suffering from inflammation type conditions, including, but not limited to, headache/migraine and inflammatory autoimmune conditions, or any other condition impacted by a disruption of the normal vagus nerve tone, including such conditions as recurrent laryngeal paralysis, traumatic brain injury, mood disorders, and nausea.

The remote controller will be body worn or carried by the user and will be programmable to deliver a biphasic asymmetric sinusoidal stimulation signal via the duel electrodes of the electrode unit 20 to the auricular branch of the vagus nerve. The controller may be configured to enable the user the ability to vary the stimulation pattern being applied but to prevent the user from altering the stimulation pattern beyond their predetermined conditions pre-set for the user. This may prevent the user from altering the waveform of the stimulus to ensure that the stimulation being applied is within acceptable limits. The controller may control the pulse rate of the stimulation and the pulse width of the stimulation.

The preferred pulse rate of the stimulation applied by the system may be around 25 Hz, with a range of between 1-200 Hz. The pulse width of the stimulation may be around 500 μs with a range varying from between about 10 μs-500 μs. It has been found that the wider the pulse rate the more preferable the body response, as the body seems to habituate at smaller pulse widths. It is difficult to maintain pulse widths greater than 500 μs, and it has been found that a pulse rate of between 400-500 μs is the "sweet spot" for activation. Similarly, the pulse amplitude should be around 0-90 mA and usually under 10 mA. An example of an optimized stimulation regime program for a patient may include applying stimulation between the stimulation sites at a frequency of 25 Hz, pulse duration of 500 μs with an alternating cycle for a period of 10 minutes.

The stimulation may be applied by the electrodes 22, 24 simultaneously to the different regions of the auricular branch of the vagus nerve. Alternatively, the stimulation may be applied sequentially by the electrodes 22, 24, or in a predetermined pattern. By targeting both the cymba conchae and the inner portion of the tragus, more targeted stimulation is achievable as the auricular branch of the vagus nerve (ABVN) supplies both of these structures.

The controller will preferably be portable and will be powered by a rechargeable or replaceable 9V power pack or battery. The duration of use may vary from user to user and will largely be dependent on the guidelines provided with the device. In another embodiment, the controller may by a dedicated software application uploaded to the user's smart phone. The user may control the electrode unit 20 by controls provided within the software application which can be regularly updated as required.

It will be appreciated that the present invention provides a system and apparatus for providing a targeted stimulation of the vagus nerve to address a number of well-established conditions. Through the use of both the cymba conchae and the inner portion of the tragus as a stimulation site, more targeted stimulation is achievable as the auricular branch of the vagus nerve (ABVN) supplies both of these structures. By targeting these locations and performing targeted stimulation between these sites, a wider range of conductivity is able to be utilized to ensure optimal stimulation.

The present invention has been found to facilitate decreases in the activity of second-order nociceptive neurons in the spinothalamic and spinoreticular tracts of the spinal cord, as well as in the trigeminal nuclear complex. Central brain projections also have a significant effect on modulating sympathetic and parasympathetic activity (or vagal tone, which when higher, is associated with an increased heart rate variability), reducing oxidative stress and stimulating the release of neurotransmitters including norepinephrine and serotonin.

Throughout the specification and claims the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features that it directly references, but also other components, steps or features not specifically listed, unless the contrary is expressly stated or the context requires otherwise.

It will be appreciated by those skilled in the art that many modifications and variations may be made to the methods of the invention described herein without departing from the spirit and scope of the invention.

The invention claimed is:

1. A system for providing transcutaneous electrical stimulation to the vagus nerve of an individual comprising:

an electrode unit having a moulded body configured to conform to the outer ear of the individual so as to be mountable entirely within the auricle of the individual, the moulded body having a first electrode positioned on a surface thereof for directly applying the transcutaneous electrical stimulation to the cymba conchae and a second electrode positioned on a surface thereof for directly applying the transcutaneous electrical stimulation to the tragus of the individual's auricle;

a controller for controlling the transcutaneous electrical impulse delivered by each of the first electrode and second electrode to facilitate stimulating both the cymba conchae and the tragus of the individual.

2. The system according to claim 1, wherein the transcutaneous electrical stimulation is applied to the auricular branch of the vagus nerve of the ear.

3. The system according to claim 2, wherein the electrical stimulation includes transmission of the electrical impulse applied to the auricular branch of the vagus nerve of the ear to central brain projections.

4. The system according to claim 1, wherein the waveform of the electrical stimulation supplied by the controller is asymmetric.

5. The system according to claim 2, wherein the waveform of the electrical stimulation supplied by the controller is biphasic.

6. The system according to claim 5, wherein the waveform of the electrical stimulation supplied by the controller is sinusoidal.

7. The system according to claim 1, wherein the controller is able to control the pulse rate of the electrical stimulation applied by the electrodes.

8. The system according to claim 7, wherein the controller is able to control the pulse width of the electrical stimulation applied by the electrodes.

9. The system according to claim 1, wherein the controller is able to control the pulse amplitude of the electrical stimulation.

10. The system according to claim 1, wherein the moulded body is made of a semi-flexible material.

11. The system according to claim 1, wherein the moulded body is formed in a variety of different sizes to accommodate different sized auricles.

12. The system according to claim 1, wherein the molded body is made of a material including silicone.

13. The system according to claim 1, wherein the moulded body includes a first and a second recess for receiving the first and second electrode respectively.

14. The system according to claim 1, wherein the moulded body has at least one projecting portion for projecting into the ear of the individual to aid in retaining the electrode unit in position.

15. The system according to claim 14, wherein the at least one projecting portion projects into the ear canal of the ear of the individual.

* * * * *